United States Patent [19]

Hautmann

[11] 4,117,110

[45] Sep. 26, 1978

[54] SOLID AIR-IMPROVING COMPOSITION

[75] Inventor: Horst Hautmann, Neuburg, Donau, Fed. Rep. of Germany

[73] Assignee: Globol Werk GmbH, Neuburg, Fed. Rep. of Germany

[21] Appl. No.: 787,532

[22] Filed: Apr. 14, 1977

Related U.S. Application Data

[63] Continuation of Ser. No. 623,118, Oct. 16, 1975, abandoned, which is a continuation-in-part of Ser. No. 458,463, Apr. 8, 1974, abandoned.

[30] Foreign Application Priority Data

Mar. 18, 1974 [DE] Fed. Rep. of Germany ....... 2412900

[51] Int. Cl.$^2$ ................................. A61L 13/00
[52] U.S. Cl. ...................... 424/76; 424/365
[58] Field of Search ............ 424/76, 365, DIG. 5, 424/63

[56] References Cited

U.S. PATENT DOCUMENTS 3,211,618  10/1965  Kambersky .................. 424/365
3,255,082  6/1966   Barton ........................ 424/76
3,818,105  6/1975   Coopersmith ............... 424/63 X

FOREIGN PATENT DOCUMENTS 2,335,111  1/1974  Fed. Rep. of Germany.

Primary Examiner—Allen J. Robinson
Attorney, Agent, or Firm—Gilbert L. Wells; Heinrich W. Herzfeld

[57] ABSTRACT

A solid air-improving composition comprising a carrier material, a volatile active material gradually evaporating therefrom and a gel formed by a paraffin component and a gelifying metal soap is improved by providing a deodorant agent or an odorant agent or a mixture of these agents as said active material, a liquid paraffin having at 20° C an evaporation number ranging from 8 to 1000 based on the evaporation number at 20° C of diethyl ether being equal one, constituting the paraffin component, the metal soap constituting the non-evaporating carrier material proper, and water in an amount sufficient for complete gelling of the metal soap and liquid paraffin; the active agent evaporates from the composition with preservation of the outer appearance of the latter but with shrinkage of its volume.

12 Claims, No Drawings

SOLID AIR-IMPROVING COMPOSITION

RELATIONSHIP TO CO-PENDING APPLICATION

This patent application is a continuation application of my pending patent application Ser. No. 623,118 filed Oct. 16, 1975 and now abandoned which is in turn a continuation-in-part of my patent application Ser. No. 458,463, filed on Apr. 8, 1974, now abandoned.

This invention relates to a solid air-improving composition comprising a carrier material, a volatile active material gradually evaporating from the carrier material, which volatile active material is a deodorant agent, an odorant agent or a mixture of these agents, and a paraffin component.

Air-improving compositions of this type have been described in German Offenlegungsschrift No. 2,335,111. The compositions described in the aforesaid publication comprise a paraffin, solid at room temperature, which has a melting point in the range of from 40° to 75° C and which may consist of paraffin wax proper, isoparaffin, ceresin, microwax, tank waxes, or mixtures of such paraffins, and, as metal soaps, for gelifying the paraffin, in particular aluminum monostearate, distearates and/or tristearates having a content of from 0 to 25%, and preferably from 3 to 7%, of free stearic acid.

These known air-improving compositions are more attractive for the user than many earlier products, because progressive evaporation of the active substances therein does not cause them to lose their shape or to shrink or to disintegrate, and their use during longer periods does not leave a shapeless, shrunken and dried-out residue. Rather, they preserve their outer shape and volume even during use for several weeks or months, appearing unchanged to the user. However they suffer from a drawback in that their evaporation rate, from which depends the length of time needed for distributing the active substance within a given space and which it takes to eliminate an undesirable odor in that space, is practically equal to the evaporation rate of the active substance or mixture of active substances in the product, so that it is not possible substantially to increase or decrease this rate of evaporation.

The same is true in the case of other known air-improving gel compositions in which the gel consists of 8 to 10% of anhydrous sodium stearate, about 64 to 67% of ethanol, 8% of 1,2-propylene glycol and 10% of water, while the balance consists of an odorant. The evaporation rate of the active substance from these gel products which have been published as formulations by Haarmann & Keimer GmbH, Holzminden, Federal Republic of Germany, is equal to the evaporation rate of the mixture of active agent and ethanol. This evaporation rate could be varied in the case of a given active agent only by a change of the alkanol component in the mixture. However, this is not possible as methanol is too toxic and higher alkanols have an undesirable inherent odor.

It is, therefore, an object of the invention to provide an air-improving composition having an evaporation rate of a given active agent therein, which rate can be varied within rather broad limits, and which composition maintains its outer appearance unchanged also during longer use, although its volume gradually decreases due to constant shrinkage.

This object is attained according to the invention by the improvement of an air-improving composition of the initially described type; which improvement comprises:

(a) said carrier material consisting essentially of sodium stearate in a concentration of about 5 to 30 percent by weight of said compositions;

(b) said paraffin agent consisting of a liquid paraffin having at 20° C an evaporation number ranging from 8 to 1000 based on the evaporation number at 20° C of diethylether being equal to 1, said paraffin agent having a concentration of about 30 to 80 percent by weight of said composition;

(c) water in an amount sufficient to form a solid gel, but less than would cause said gel to melt at a temperature below 40° C or stated another way, the solidification point is not less than about 40° C;

(d) said deodorant material is selected from these deodorant materials described on pages 11 to 14 of German Patent No. 2,335,111, and (e) said odorant is selected from these odorants described on pages 15 to 20 of the aforesaid German Patent;

said deodorant agent or odorant agent or mixture of such agents being present in said composition in an amount effectively improving the air in a closed room, whereby, while said volatile active material gradually evaporates from said composition in gel form, the latter undergoes shrinkage of its volume while preserving its outer appearance and configuration.

Preferably, the sodium stearate constitutes from 5 to 30% of the total weight of the composition. The sodium stearate used is advantageously a technical sodium stearate containing such a proportion of free stearic acid that its pH-value is not higher than 9. The proportion of free stearic acid should not exceed 25% of the weight of the stearate and should preferably lie between 2 and 7% of the latter.

Advantageously, the proportion of liquid paraffin is 30 to 80%, calculated on the total weight of the composition. Its evaporation number at 20° C, based on that of diethyl ether at 20° C being one, is preferably from 30 to 120, and optimally 50 to 65 in the case of an evaporation surface of 30 to 40 cm².

Liquid paraffins which possess these preferred evaporation numbers are above all those having isoparaffinic structure, but also such liquid normal paraffins as n-nonane, n-decane, n-undecane, n-dodecane and n-tridecane.

In order to assure a possibility of simple production, the composition preferably contains an agent for lowering the solidification temperature of the composition, which agent should be present in sufficient amount, so that the solidification temperature of the composition is below 60° C, and preferably in the range from 50° to 65° C. A liquid low molecular glycol, preferably 1,2-propylene glycol, is especially suitable as such agent. An admixture of 5 to 15% by weight of ethanol or isopropanol facilitates the dissolution of the perfume in the composition according to the invention. It also contributes somewhat to the lowering of the solidification temperature of the composition to the aforesaid desirable temperature range.

The boiling point of paraffins, suitable for use in the compositions of the invention, especially of those having isoparaffinic structure, lies preferably between 100° and 260° C, and their solidification temperature lies below minus 30° C. Paraffins having a boiling point between 140° and 200° C are especially preferred.

Paraffins suitable for use in the compositions according to the invention which have evaporation numbers as given above and whose solidification temperatures and boiling points preferably lie within the limits stated hereinbefore, are primarily isoparaffins having 8 to 14 atoms per molecule, their evaporation number being the higher, the lesser the branching of the paraffin chain. Normal paraffins may also be used, wherein the number of carbon atoms per molecule has to be lower than the number of carbon atoms per molecule of the corresponding isoparaffin having the same evaporation number. Isoparaffins having evaporation numbers of 8, 36, 50, 65, 107 and 680 are readily commercially available (Isopar E to M, Solvent ID, Shellsol T).

The active component, i.e. a deodorant, an odorant or a mixture thereof should be present in an amount of about 10%, a minimum of 5% and a maximum of 20% by weight being the preferred limits, depending largely on the shape and volume of the "gel stick" in which form these compositions are usually molded.

Suitable deodorants as well as those of their decomposition products which are neither toxic nor irritate the eyes and lungs are in particular aliphatic, cycloaliphatic and araliphatic, olefinically unsaturated alcohols or esters or aliphatic, cycloaliphatic and aromatic aldehydes or mixtures of such compounds which are compatible with each other. Such suitable deodorants are described on pages 11 to 14 of the German Patent No. 2,335,111. The term "deodorant" is used herein as defined at the bottom of page 9 and the top of page 10 of the last-mentioned German Patent.

These deodorants preferably consist of a volatile aliphatic, cycloaliphatic or araliphatic olefinically unsaturated alcohol or ester, or an aliphatic, cycloaliphatic, or aromatic aldehyde or of mixtures of these with one another.

Aliphatically unsaturated alcohols which can be used in the preparations according to the invention as deodorant include for example: nonadienol, methylheptenol, dimethylheptenol, dimethyloctenol, 3-methyl-3-penten-1-ol, undecylenol, cis-3-hexen-1-ol, trans-2-hexen-1-ol.

Cycloaliphatic unsaturated alcohols which can be used as deodorant in the preparations according to the invention include for example: linalol, ethyllinalol, ocimenol, myrcenol, dihydromyrcenol, myrtenol, geraniol, methylgeraniol, ethylgeraniol, bisabolol, nerolidol, coniferol, dihydromyrcenol, elemol, farnesol, cedrenol, terpineols, such as 4-terpineol, -terpineol, terpineols, nopol, and furfuryl alcohols.

Araliphatic olefinically unsaturated alcohols which can be used as deodorant in the compositions according to the invention are e.g.: cinnamyl alcohol, homocinnamyl alcohol and amylcinnamyl alcohol.

Esters which can be used as deodorants in the compositions according to the invention are (a) esters fromed from an olefinically saturated aliphatic, cycloaliphatic or aromatic acid residue and an olefinically unsaturated aliphatic, cycloaliphatic or aromatic alcohol moiety such as e.g.: esters formed between olefinically unsaturated alcohols and formic acid, acetic acid, propionic acid, butyric acid, isobutyric acid, valeric acid, hexylic acid, heptylic acid, octylic acid, undecylic acid, malonic acid, or benzoic acid, (b) esters which are formed between an olefinically unsaturated aliphatic, cycloaliphatic or aromatic acid residue and an olefinically saturated or unsaturated aliphatic, cycloaliphatic or aromatic alcohol residue, such as e.g.: esters formed between unsaturated alcohols and maleic acid, fumaric acid, acrylic acid, 2,3-dimethylacrylic acid, methacrylic acid, aconitic acid, tiglic acid, angelica acid, sorbic acid, crotonic acid, dimethylcrotonic acid, furylacrylic acid, 2-decenylenic acid, undecylenic acid, cinnamic acid.

Such esters are e.g.: formic or acetic acid 2-hexenyl ester, -3-nonenyl ester, -3-hexenyl ester, -dimethylheptenyl ester, -geranyl ester, citronellyl ester, -linalyl ester, -ethyllinalyl ester, -terpinyl ester, -nopyl ester, -eugenyl ester, -cinnamyl ester, -amylcinnamyl ester; propionic acid propyl ester, -linalyl ester, -cinnamyl ester; butyric acid or isobutyric acid 2-hexenyl ester, -3-hexenyl ester, -cinnamyl ester; capric acid 3-hexenyl ester; undecylenic acid allyl ester; methylheptincarbonate and dimethylfumarate, diethylfumarate and diallylfumarate; acrylic acid 2-ethylhexyl ester; 2,3-dimethylacrylic acid n-butyl ester; methacrylic acid n-ethyl ester, -n-butyl ester, -2-ethylhexyl ester, -phenylethyl ester, -ethylpiperonyl ester; tiglic acid n-butyl ester, -geranyl ester, -cinnamyl ester, -benzyl ester, -phenylethyl ester; angelica acid ethyl ester, -n-butyl ester, -iso-butyl ester, -isoamyl ester; allylsorbate; ethylcrotonate, geranylcrotonate and benzylcrotonate; 2,3-dimethyl-crotonic acid benzyl ester; furylacrylic acid n-butyl ester, -isobutyl ester; 2-decenylenic acid n-butyl ester; undecylenic acid allyl ester, -phenylethyl ester, -allyl ester, -n-butyl ester, -phenylethyl ester or -benzyl ester.

Aliphatic aldehydes which can be used as deodorants for the compositions according to the invention are e.g.: n-hexenal, n-heptanal, n-octanal, 2,4-hexadienal, nonadienal, 2-nonanal, 2-nonenal, n-nonanal, n-decanal, n-undecanal, 2-tridecenal, methylnonylacetaldehyde, 10-undecen-1-al, dodecanal, tridecanal, myristic aldehyde, 3,3,5-trimethylhexanal, methylheptylacetaldehyde, methylhexylacetaldehyde, methyloctylacetaldehyde.

Cycloaliphatic aldehydes which can be used as deodorants in the compositions according to the invention are e.g.: citral, neral, ethylcitral, iso-cyclocitral, phellandral, lilial, citronellal, -methylene-citronellal, hydroxycitronellal, dihydrocitronellal, methylsafranal, dihydrolavandulyl aldehyde, 4(4-methyl-3-penten-1-yl)-3-cyclohexen-1-carboxaldehyde and -(4-methylcuclohexyl)-butyraldehyde, citronellyloxyacetaldehyde and geranyloxyacetaldehyde.

Aromatic aldehydes which can be used in the compositions according to the invention as deodorants are e.g.: benzaldehyde, phenylacetaldehyde, benzylacetaldehyde, para-tolylacetaldehyde, para-iso-propylphenylacetaldehyde, anisaldehyde, para-ethoxybenzaldehyde, cinnamonaldehyde, butyl- -methylhydrocinnamonaldehyde, heliotropine, diisopropylbenzaldehyde, veratraldehyde, -methylcinnamonaldehyde, amylcinnamonaldehyde, isoamylcinnamonaldehyde, hexylcinnamonaldehyde, vanillin, -methyl-para-isopropylcinnamonaldehyde, -methyl-para-isopropylhydrocinnamonaldehyde, para-iso-propylbenzylbutyraldehyde, para-methyl- -phenylpropionaldehyde, cyclamenaldehyde, -(para-isopropylphenyl)-propionaldehyde, -phenylpropionaldehyde, phenoxyacetaldehyde, cuminaldehyde, salicylaldehyde and furaldehyde.

Odorants suitable for use in the compositions according to the invention are defined and described on pages 15 to 20 of the last-mentioned German Patent.

The air-improving effect of the compositions according to the invention sets in especially rapidly in a closed room such as, for instance, a room as described on page 9 of the German Patent No. 2,335,111.

Under the term odorant there are to be understood chemically exactly defined individual compounds which are either present in ethereal oils or can be made from these by chemical conversion or which can also be synthetised from other chemicals.

Preferred for the compositions according to the invention are those odorants which smell pleasant, which do not weaken the sense of smell and are not toxic under the conditions of use for men and animals and which do not irritate the eyes and lungs.

Odorants which are used in the compositions according to the invention are for example aliphatic, cycloaliphatic or araliphatic saturated alcohols or esters, terpenic and/or cycloaliphatic, aromatic hydrocarbons or heterocyclic compounds, aliphatic, cycloaliphatic or aromatic ethers, acetals or ketones as well as phenols or mixtures of such compatible compounds.

Alcohols which are suitable as odorants for the composition according to the invention are for example: 1-heptanol, 1-octanol, 1-nonanol, 3-nonanol, 1-decanol, dimethyloctanol, 2-hexyl-hexanol, hendecyl alcohol, para-iso-propyl-cyclo-hexanethanol, trimethylcyclohexanol, 1-undecanol, tetrahydrogeraniol, dihydro--terpineol, dihydro-terpinenol, -borneol, iso borneol, dihydrocyclol, fenchylalcohol, benzylalcohol, phenylethylalcohol, 3-phenylpropylalcohol, anisylalcohol, phenylhexylalcohol, methylphenylcarbinol, dimethylbenzylcarbinol, diethylbenzylcarbinol, phenylacetildimethylcarbinol, cyclamenalcohol.

Esters which are suitable as odorants for the composition according to the invention are e.g.: the heptyl, methyl, phenylethyl, benzyl and citronellyl esters of formic acid; acetic acid heptyl ester, acetic acid-nonandiol-1,3-diester, acetic acid -ortho-tert. butylcyclohexyl ester and the trimethylcyclohexyl, 1-bornyl, iso-bornyl, anisyl, tert. butylcyclohexyl, dihydrocyclyl dihydroterpinyl, para-methyl-phenylethyl, phenylethyl, benzyl, isobutylphenyl, menthyl and phenyl esters of acetic acid; the anisyl, benzyl, phenylethyl and isobornyl esters of propionic acid; acetic acid phenylethylphenyl ester, ethylaceto-acetate; the isoamyl, ethyl- -hydroxyl--methyl and benzyl esters of butyric acid; epoxypropionic acid methylphenyl ester and the isoamyl, phenoxyethyl and phenylethyl esters of isobutyric acid; isovalerianic acid benzyl ether, ethylheptate, ethyloctate, ethylnonate, ethylpelargonate, n-propylcaprate; methyl undecylate; dipropylmalonate; dipropylsuccinate, isoamylsuccinate; the n-butyl, methyl, ethyl and amyl esters of benzoic acid; the methyl, ethyl, amyl, isoamyl and benzyl esters of salicyclic acid; methylanthranilate.

Hydrocarbons and heterohydrocarbons which are suitable as odorants for the compositions according to the invention are e.g.: camphene, -pinene, -pinene, myrcene, -phellandrene, -phellandrene, ocimene, dipentene, norbornadiene, paracymol, terpinols, nerol, bisaboles, sylvestrene, citronellols, fenchene, cedrene and caryophyllene;

Dicyclohexyl, diphenyl, diphenylmethane, methyldiphenylmethane, diphenylethane, xylene, musk or quinoline.

Ethers which are suitable as odorants for the compositions according to the invention are e.g.: iso-butylheptylether, methyl-n-hexylether, iso-propylheptylether, ethyllinalylether, ethylgeranylether, 1,8-cineol, ethylbenzylether, methylphenylethylether, n-propylbenzylether, iso-butylbenzylether, butylbenzylether, iso-amylbenzylether, anetol, dihydroanetol, hexylbenzylether, diphenylether, methyldiphenylether, -naphtolmethylether, -naphtolethylether, estragol, 2-methyl-5-isopropenylanisol, safrol, anisol, para-acetanisol, acetiso-eugenol, aceteugenol, menthol, ambrette musk and roseether.

Ketones which are suitable as odorants for the compositions according to the invention are e.g.: ethylamylketone, 3-nonanon, methyl-iso-hexylketone, 2-methylheptenone, jasmone, dihydrojasmone, isojasmone, carvone, 2-cyclohexylhexanone, p.-octylcyclohexanone, 1,1,7-trimethylbicyclo-1,1,3-hepten-1-one, 1,1,3-trimethyl-2-cyclohexanone-4, p.-tert. butylcyclohexanone, isophorone, 1-carvone, ethylgeranylacetone, fenchone, hexa-hydropseudoionone, diisopropylacetophenone, acetophenone, benzylacetone, -hexylidene-cyclopentenone, muscone, benzophenone, coumarine, cyclopenta-decanone, -ionone, allylionone, -ionone, menthone, pulegone, parahydroxy-phenyl-2-butanone and musk ketone.

Acetals which are particularly suitable as odorants in the compositions according to the invention are e.g.: phenylacetal, dehydrodimethylacetal, hydroxycitronellal-dimethylacetal, 2-nonyn-1-al-dimethylacetal.

Phenols which are suitable as odorants for the compositions according to the invention are e.g.: thymol, carvacrol, chavicol, o.-ethoxyphenol, guaiacol, eugenol, iso-eugenol, 5-propenyl-2-ethoxyphenol.

These phenols can optionally also serve as stabilising agents for the volatile active substance components.

The reason for this prompt air-improving effect may be seen in a rapid diffusion of comparatively small and therefore light particles of perfume and paraffin which diffusion occurs in the solid composition and evaporation from the surface of the latter, whereby these particles are dispersed rather rapidly and evenly in the whole room. The above-mentioned paraffins are commercially available in a highly purified state; they are, therefore, practically non-toxic and are also used in cosmetics and drugs. In contrast to the rate of evaporation of active agent from the known compositions described hereinbefore, which are either based on paraffins, which are solid at room temperature and in mixture with aluminum stearates, or which are compositions of sodium stearate and ethanol, the evaporation rates, and thereby the distribution velocity in a given room, of active agents present in the compositions according to the invention can be varied, i.e., increased or decreased by means of a corresponding choice of a liquid paraffin having suitable evaporation number.

Generally, the amount of water present for complete gelling in the compositions according to the invention should be at least 2% based on the total weight of the composition and should not surpass 20% as, otherweise, the solidification temperature of the composition would be too low (this temperature of the composition should preferably not be below 40° C). A proportion of from 5 to 10% by weight of water in the composition is preferred.

The content of odorant, deodorant or mixtures of both in the compositions according to the invention is maximally 62%, such compositions containing the minimum amounts of 5% of sodium stearate, 30% of liquid paraffin and 3% of water, all percentages being by weight.

The compositions according to the invention are preferably prepared by producing the sodium stearate in situ from stearic acid and a stoichiometrically required amount of caustic soda when admixing these two reagents with the liquid paraffin. These two reaction components can be more easily admixed with the liquid paraffin than the commercially available sodium stearate. Besides, it is thus possible to determine exactly the desired surplus of stearic acid which prevents the pH-value of the resulting mixture from being too high, i.e. above 9.

In the manufacturing process, liquid paraffin and the free stearic acid are first charged into a closed reaction vessel and heated with stirring at 65° C until a clear solution of stearic acid in paraffin is obtained.

In a second vessel set in a cooling bath, water, caustic soda and 1,2-propylene glycol are mixed with stirring, and the resulting mixture is added to the hot solution in the first reaction vessel with rapid stirring. Because of the commencing saponification of the stearic acid, the temperature of the mixture rises to about 75° C. In most cases, the deodorants and odorants being at room temperature can now be directly added with stirring, and the mixture, which has still a temperature of about 65° C, is then poured into molds. For example, cylindrical molds with an inside diameter of 65 mm are each filled with exactly 75 g of the ready mixture.

Air-improving compositions described in the following examples can be produced by the manufacturing process described above; these non-limitative examples serve to illustrate the invention (amounts are given in parts by weight).

| Example | 1 | 2 | 3 | 4 | 5 | 6 |
|---|---|---|---|---|---|---|
| stearic acid | 12,0 | 12,0 | 12,0 | 12,0 | 12,0 | 12,0 |
| isoparaffin having an evaporation number of 8 | 60,0 | | | | | |
| (Isopar G) 36 | | 60,0 | | | | |
| 50 | | | 60,0 | | | |
| 65 | | | | 60,0 | | |
| 107 | | | | | 60,0 | |
| 680 | | | | | | 60,0 |
| water | 5,0 | 5,0 | 5,0 | 5,0 | 5,0 | 5,0 |
| 1,2-propylene gylcol | 6,0 | 6,0 | 6,0 | 6,0 | 6,0 | 6,0 |
| caustic soda | 2,1 | 2,1 | 2,1 | 2,1 | 2,1 | 2,1 |
| odorant e.g. bergamotte oil | 17,0 | 17,0 | 17,0 | 17,0 | 17,0 | 17,0 |

The "evaporation number" of paraffins is the quotient of $$\frac{\text{evaporation time of 1 weight unit of paraffin}}{\text{evaporation time of 1 weight unit of diethyl ether}}$$

measured at 20° C. [DIN (German Industrial Standard) 53 170]

| Example | 7 | 8 | 9 | 10 |
|---|---|---|---|---|
| Isopar G | 69.1 | 66.1 | 51.1 | |
| n-decane | | | | 66.1 |
| stearid acid | 12.0 | 12.0 | 12.0 | 12.0 |
| sodium hydroxide (anhydrous) | 1.9 | 1.9 | 1.9 | 1.9 |
| water (deionized) | 2.0 | 5.0 | 20.0 | 5.0 |
| 1,2-propylene glycol | 5.0 | 5.0 | 5.0 | 5.0 |
| rose perfume | 10.0 | 10.0 | 10.0 | 10.0 |
| Solidification point | 65° C | 50° C | 40° C | 58° C |

| Example | 11 | 12 | 13 | 14 | 15 |
|---|---|---|---|---|---|
| Isopar G | 59.1 | 61.1 | 46.1 | | 56.1 |
| n-decane | | | | 56.1 | |
| stearic acid | 12.0 | 12.0 | 12.0 | 12.0 | 12.0 |
| sodium hydroxide (anhydrous) | 1.9 | 1.9 | 1.9 | 1.9 | 1.9 |
| water (deionized) | 2.0 | 4.0 | 20.0 | 4.0 | 4.0 |
| 1,2-propylene glycol | 5.0 | 5.0 | 5.0 | 5.0 | 5.0 |
| isopropanol | 10.0 | 10.0 | 10.0 | 10.0 | |
| ethanol | | | | | 10.0 |
| rose perfume | 10.0 | 5.0 | 15.0 | 10.0 | 10.0 |
| Solidification point | 60° C | 50° C | 40° C | 50° C | 50° C |

The gels according to the invention which are based on odourless liquid paraffin, the gel structure of which is supplied by sodium stearate combines in an ideal way relatively low cost of production with high efficacy of freshening the air in a closed room. This is due to the fact that the perfume and the liquid paraffin evaporate simultaneously. Owing to this "coevaporation" the perfume is dispersed rapidly and evenly over the whole room to be air-freshened.

When the major portion of the air-freshening composition consists of water the particles dispersed in the room consist of hydratized perfume molecules which are considerably larger than the perfume paraffin particles evaporating from the gel composition according to the invention. Therefore hydratized perfume particles need much more time to get dispersed over a given room when no means for air circulation are provided. Another advantage of the composition according to the invention results in the fact that no emulsifier is required. Moreover, there is no need to match the rate of evaporation of the perfume to that of the gel or more exactly the paraffin. On the contrary, perfumes whose evaporation rates differ over a broad range may be used in the composition of the invention by choosing a paraffin of suitable evaporation number.

I claim:

1. A solid molded air improving gel composition comprising:
   (a) a carrier material consisting of sodium stearate in a concentration of about 5 to 30 percent by weight of said composition;
   (b) water in an amount of from at least 2% required for complete gelling; up to not more than about 20% by weight of said composition;
   (c) a volatile component comprising
      ($c_1$) a liquid paraffin having at 20° C an evaporation number ranging from 8 to 1000 based on the evaporation number at 20° C of diethylether being equal to 1, said liquid paraffin having a concentration of about 30 to 80 percent by weight of said composition; and
      ($c_2$) a volatile deodorant or odorant material in an amount of not more than 62%, based on the weight of said composition, whereby the solidification point of said composition is not less than about 40° C, being sufficient to effectively deodorize or odorize the air in a closed room of determined space.

2. The composition as described in claim 1, wherein said liquid paraffin is an isoparaffin.

3. The composition as described in claim 1, wherein said liquid paraffin has at 20° C an evaporation number ranging from 30 to 120 based on the evaporation number at 20° C of diethyl ether being equal to one.

4. The composition as described in claim 1, wherein said liquid paraffin has at 20° C an evaporation number ranging from 50 to 65, based on the evaporation number at 20° C of diethyl ether being equal to one.

5. The composition as described in claim 1, in such proportion that said sodium stearate is a technical product containing free stearic acid, whereby the pH-value of the stearate is not higher than 9.

6. The composition as described in claim 5, wherein the proportion of free stearic acid contained in the sodium stearate does not exceed 25% based on the weight of the sodium stearate.

7. The composition as described in claim 1, wherein the solid air-improving composition further contains an agent for lowering the solidification temperature of the composition, consisting essentially of a liquid glycol.

8. The composition as described in claim 7, wherein the amount of said liquid glycol is sufficient to adjust the solidification temperature of said composition to less than 60° C.

9. The composition as described in claim 7, wherein said agent for lowering the solidification temperature is 1,2-propylene glycol.

10. The composition as described in claim 1, wherein the boiling point of said liquid paraffin is between 100° and 260° C and the solidification temperature of said liquid paraffin is less than minus 30° C.

11. The composition as described in claim 10, wherein the boiling point of said liquid paraffin is between 140° and 200° C.

12. The composition as described in claim 1, wherein the porportion of water in the composition amounts to from 5 to 10%, based on the total weight of the composition.

* * * * *